US005147875A

United States Patent [19]

Coates et al.

[11] Patent Number: 5,147,875

[45] Date of Patent: Sep. 15, 1992

[54] 2-(SUBSTITUTED PHENYL)-4-OXO-QUINAZOLINES

[75] Inventors: William J. Coates, Welwyn Garden City, England; Lawrence I. Kruse, Malvern, Pa.

[73] Assignee: Sanshin Kogyo Kabishiki Kaisha, Japan

[21] Appl. No.: 443,986

[22] Filed: Nov. 30, 1989

[30] Foreign Application Priority Data

Nov. 30, 1988 [GB] United Kingdom ................ 8827988

[51] Int. Cl.[5] .................. A61K 31/505; C07D 239/91

[52] U.S. Cl. .................................. 514/259; 544/288; 544/289; 564/154; 564/155; 564/158

[58] Field of Search ................ 544/289, 288; 514/259

[56] References Cited

U.S. PATENT DOCUMENTS

| | | | |
|---|---|---|---|
| Re. 26,565 | 4/1969 | Rodgers et al. | 544/289 |
| 3,169,129 | 2/1965 | Rodgers et al. | 544/289 |
| 3,526,627 | 9/1970 | Brooks, Jr. | 544/289 |
| 3,651,061 | 3/1972 | Ericsson et al. | 544/289 |
| 4,159,330 | 6/1979 | Doria et al. | 544/289 |

FOREIGN PATENT DOCUMENTS

| | | |
|---|---|---|
| 58822 | 9/1982 | European Pat. Off. . |
| 1523081 | 8/1978 | United Kingdom . |

OTHER PUBLICATIONS

Koizumi et al., JP–A 52/51378 Chem. Abstr. 87:201571g (1977).

Subrahmanyam et al., "Benziosoxazolium Cations–II, Tetrahedron," 29, 3173 (1973).

*Primary Examiner*—C. Warren Ivy
*Assistant Examiner*—James H. Turnipseed

[57] ABSTRACT

This invention relates to quinazolinone derivatives which have bronchodilator activity. A compound of the invention is 2-(2-propoxyphenyl)quinazolin-4(3H)-one.

9 Claims, No Drawings

2-(SUBSTITUTED PHENYL)-4-OXO-QUINAZOLINES

The present invention relates to quinazolinone derivatives. This invention further relates to intermediates in their preparation, pharmaceutical compositions containing them and a method of effecting bronchodilatation by administering them. The compounds of this invention are inhibitors of a calmodulin insensitive cyclic GMP phosphodiesterase and are of use in combatting conditions where such inhibition is thought to be beneficial. They are bronchodilators and are therefore of use in combatting chronic reversible obstructive lung diseases such as asthma and bronchitis. Furthermore they are vasodilators and are therefore of value in combatting angina, hypertension and congestive heart failure.

Japanese patent application no. 52-51378 discloses compounds of the general formula (A):

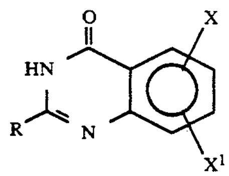

(A)

wherein R is an alkyl, styryl, lower alkoxy, nitro, halo or a substituted phenyl group, and X and $X^1$ which may be the same or different are hydrogen, halo, nitro or lower alkyl. These compounds are described as being of value as pharmaceutical products such as bactericidal and miticidal agents or as intermediates in the synthesis thereof. 2-(2-Ethoxyphenyl)quinazolin-4(3H)-one is specifically disclosed.

U.S. Pat. No. 3,169,129 discloses compounds of the general formula (B):

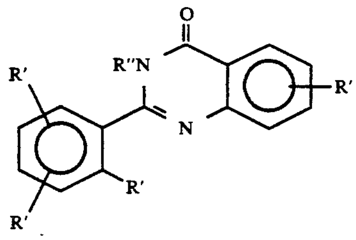

(B)

wherein R′ represents hydrogen or a substituent such as halogen, hydroxy, $C_{1-4}$alkyl or $C_{1-4}$alkoxy and R″ is hydrogen or $C_{1-4}$alkyl. These compounds are described as having useful fluorescent properties. Although 2-(2-methoxyphenyl)quinazolin-4(3H)-one is specifically disclosed, there is no suggestion of pharmacological activity.

According to the present invention there is provided compounds of the formula (1):

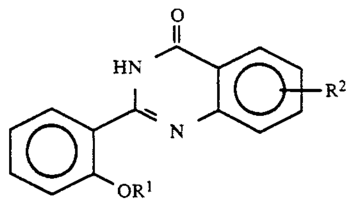

(1)

and pharmaceutically acceptable salts thereof, wherein $R^1$ is $C_{1-6}$alkyl, $C_{2-6}$alkenyl, $C_{3-5}$cycloalkyl$C_{1-4}$alkyl, phenyl$C_{1-4}$alkyl or $C_{1-4}$alkyl substituted by 1 to 6 fluoro groups;

$R^2$ is hydrogen, $C_{1-6}$alkyl, $C_{1-6}$alkylthio, $C_{1-6}$alkoxy, nitro or $-NR^3R^4$; and $R^3$ and $R^4$ are independently hydrogen or $C_{1-4}$alkyl optionally substituted by hydroxy provided that the carbon atom adjacent to the nitrogen atom is not substituted by hydroxy;

with the proviso that $R^1$ is not methyl or ethyl when $R^2$ is hydrogen.

Suitably $R^1$ is $C_{2-5}$alkyl for example ethyl, n-propyl, isopropyl, butyl, isobutyl or pentyl.

Suitably $R^1$ is $C_{3-5}$alkenyl for example allyl, butenyl or pentenyl.

Suitably $R^1$ is cyclopropylmethyl or benzyl.

Examples of $C_{1-4}$alkyl substituted by 1 to 6 fluoro groups include $-CF_3$, $-CH_2CF_3$ or $-CF_2CHFCF_3$.

Preferably $R^1$ is n-propyl.

Suitably $R^2$ is hydrogen or $C_{1-6}$alkyl for example methyl or ethyl.

Suitably $R^2$ is $C_{1-6}$alkylthio or $C_{1-6}$alkoxy for example methylthio, ethylthio, methoxy or ethoxy.

Suitably $R^2$ is nitro or $-NR^3R^4$ for example methylamino, dimethylamino or 2-hydroxyethylamino.

Particular compounds of this invention are:

2-(2-propoxyphenyl)quinazolin-4(3H)-one,
7-methylthio-2-(2-propoxyphenyl)quinazolin-4(3H)-one,
7-nitro-2-(2-propoxyphenyl)-4(3H)-quinazolinone,
7-amino-2-(2-propoxy-phenyl)-4(3H)-quinazolinone, or
7-methylamino-2-(2-propoxyphenyl)-4(3H)-quinazolinone or pharmaceutically acceptable salts thereof.

This invention covers all tautomeric and optical isomeric forms of compounds of formula (1).

Compounds of the formula (1) may form pharmaceutically acceptable salts with metal ions, such as alkali metals for example sodium and potassium, or with an ammonium ion.

Compounds of the formula (1) wherein $R^2$ is $-NR^3R^4$ may form pharmaceutically acceptable salts with acids such as hydrochloric, hydrobromic, sulphuric and phosphoric acids.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, sublingually, parenterally, transdermally, rectally, via inhalation or via buccal administration.

Compounds of formula (1) and their pharmaceutically acceptable salts which are active when given orally or via buccal administration can be formulated appropriately in dosage forms such as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include starch, celluloses, lactose, sucrose and magnesium stearate. Where the composition is in the form of a capsule, any routine encapsulation process may be suitable, for example using the aforementioned carriers in a hard gelatin capsule shell. Where the composition is in the form of a soft gelatin shell capsule, any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene glycol, polyvinylpyrrolidone, 2-pyrrolidone, cyclodextrin, lecithin, arachis oil or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required, for example from 1 to 8 times a day or by infusion. The compositions of the invention are bronchodilators and are useful in chronic reversible obstructive lung disease for example asthma and bronchitis. The compositions of the present invention have vasodilator activity and are of use in the treatment of angina, hypertension and congestive heart failure. Such conditions can be treated by administration orally, sublingually, topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a single pharmaceutical composition. Examples of compounds which may be included in pharmaceutical compositions with the compounds of the formula (1) are bronchodilators such as sympathomimetic amines for example isoprenaline, isoetharine, salbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) and pharmaceutically acceptable salts thereof can be prepared by a process which comprises cyclising a compound of the formula (2):

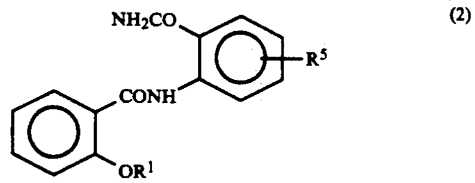

wherein $R^1$ is as hereinbefore defined, and $R^5$ is a group $R^2$ as hereinbefore defined or a precursor thereof and thereafter where necessary:

- converting a group $R^5$ to a group $R^2$;
- optionally forming a pharmaceutically acceptable salt thereof.

Suitably the cyclisation of a compound of the formula (2) is performed in the presence of a base such as aqueous sodium hydroxide or potassium hydroxide optionally with a co-solvent such as pyridine, tetrahydrofuran, dioxane or dimethylformamide at ambient or elevated temperatures for example 20°–150° C., preferably at the reflux temperature of the reaction mixture.

An example of $R^5$ being a precursor to a group $R^2$ is when $R^5$ is a nitro group. Such a group can be converted to an amino group by treatment with a reducing agent, for example by catalytic hydrogentation.

A compound of the formula (1) wherein $R^2$ is amino can be converted to a $C_{1-4}$alkylamino group under reductive amination conditions, for example by reaction with a suitable aldehyde or ketone such as acetaldehyde or acetone in the presence of a reducing agent such as sodium borohydride, or by reaction with a suitable orthoformate such as trimethylorthoformate followed by reaction with a reducing agent such as sodium borohydride.

A compound of the formula (2) can be prepared by reaction of a compound of the formula (3):

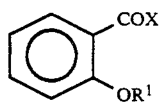

(3)

wherein X is halo, and $R^1$ is as hereinbefore defined, with a compound of the formula (4):

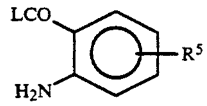

(4)

wherein L is amino or $C_{1-4}$alkoxy and $R^5$ is as hereinbefore defined, and thereafter, when L is $C_{1-4}$alkoxy, by reaction with ammonia.

Suitably the reaction of compounds of the formulae (3) and (4) is performed at ambient or elevated temperature e.g. 20°-100° C. in a solvent such as acetone, toluene or tetrahydrofuran in the presence of a base such as triethylamine, pyridine, aqueous sodium hydroxide or aqueous sodium acetate. Preferably the reaction is performed at ambient temperature in acetone or tetrahydrofuran in the presence of a mixture of acetic acid and aqueous sodium acetate. Suitably X is bromo or chloro.

A compound of the formula (3) can be prepared by reaction of a compound of the formula (5):

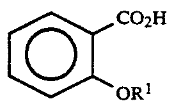

(5)

wherein $R^1$ is as hereinbefore defined, with a suitable halogenating agent. Suitable halogenating agents include thionyl chloride or phosphorous tribromide.

Pharmaceutically acceptable base addition salts of the compounds of the formula (1) may be prepared by standard methods, for example by reacting a solution of the compound of the formula (1) with a solution of the base.

Pharmaceutically acceptable acid addition salts of the compounds of the formula (1) wherein $R^2$ is $-NR^3R^4$ may be prepared from the corresponding base of the compounds of the formula (1) in conventional manner. For example the base may be reacted with an acid in a $C_{1-4}$alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

In another aspect the present invention provides pharmaceutical compositions comprising a compound of the formula (1) as hereinbefore defined or 2-(2-methoxyphenyl)quinazolin-4(3H)-one or a pharmaceutically salt thereof and a pharmaceutically acceptable carrier.

In a further aspect the present invention provides a method of effecting bronchodilatation in a host in need thereof by administration of a non-toxic but effective amount of a compound of the formula (1) as hereinbefore defined, 2-(2-methoxyphenyl)quinazolin-4(3H)-one or 2-(2-ethoxyphenyl)quinazolin-4(3H)-one or a pharmaceutically acceptable salt thereof.

2-(2-Methoxyphenyl)quinazolin-4(3H)-one and 2-(2-ethoxyphenyl)quinazolin-4(3H)-one can form pharmaceutically acceptable salts, be formulated as pharmaceutical compositions and be used as medicaments as hereinbefore described for compounds of the formula (1).

The following biological test method, data and Examples serve to illustrate this invention.

Bronchodilatation - In vivo

Male guinea-pigs of the Dunkin Hartley strain (500-600 g) were anaesthetised with Sagatal (pentobarbital sodium) (60 mg/kg). Airway resistance was measured using a modification of the classical Konzett-Rossler technique (Versuchsanordnung zu Untersuchungen an der Bronchialmuskulatur. Naunyn-Schmiedebergs Arch. Exp. Path. Pharmak., vol 195: pp 71-74, (1940)). U46619 (9,11-methanoepoxy-$PGH_2$) was infused i.v. at a rate of 2.5 nmol/min, this produced a steady state of broncho-constriction (approximately 120% increase from basal airway resistance). The compound under test was administered by i.v. bolus injection, and the subsequent peak inhibition of bronchoconstriction recorded.

Administration of the compound of Example 1 (10 μmol/kg) reduced the U46619-induced broncho-constriction by 34%. This result demonstrates in vivo anti-bronchoconstrictor activity.

Phosphodiesterase Activity

The activity of the compounds of the present invention as inhibitors of a calmodulin insensitive cyclic GMP phosphodiesterase was measured using the procedure described in European Patent Application No. 293063. The compounds of Examples 1 to 5 had $IC_{50}$ values (the concentration of inhibitor required for 50% inhibition of enzyme activity) in the range 0.71 to 5.30 μM. The compounds of the present invention have the advantage that they are selective in not inhibiting cyclic AMP phosphodiesterase (type III).

EXAMPLE 1

2-(2-Propoxyphenyl)quinazolin-4(3H)-one a) A mixture of 2-propoxybenzoic acid (5 g) in thionyl chloride (20 ml) was heated under reflux for three hours. Thionyl chloride was removed under reduced pressure and the residue was azeotroped with toluene to yield the acid chloride as a yellow oil (5.5 g). A solution of anthranilamide (3.77 g) in a mixture of saturated aqueous sodium acetate (20 ml) and acetic acid (20 ml) was added to the yellow oil in acetone (4 ml). The resulting solution was stirred at ambient temperature for one hour to yield as a light brown precipitate 2-(2-propoxybenzamido)benzamide, 3.78 g. A sample recrystallised from ether had m.p. 149°-150° C.

b) 2-(2-Propoxybenzamido)benzamide (2.73 g) was added to a refluxing mixture of 2 Normal aqueous sodium hydroxide (55 ml) and pyridine (2 ml). The resulting solution was stirred under reflux for 15 minutes and was then poured onto ice (150 ml) and acidified with concentrated hydrochloric acid to yield a sample of the title compound, 2.28 g, m.p. 88°-89° C. This together with another sample (0.77 g) similarly prepared was recrystallised from ethanol/water to yield the pure title compound as a white solid, 2.57 g, m.p. 89°-90° C.

EXAMPLE 2

7-Methylthio-2-(2-propoxyphenyl)quinazolin-4(3H)-one a) Methyl mercaptan was bubbled through a solution of copper sulphate pentahydrate (50 g) in water (200 ml) for 30 minutes to form cuprous thiomethoxide (11.70 g) as a precipitate, which was collected and washed successively with water, methanol and ether.

A solution of sodium nitrite (3.70 g) in water (15 ml) was added with cooling (3°-4° C.) to a stirred suspension of 4-amino-2-nitrobenzoic acid (9.11 g) in water (50 ml) and concentrated sulphuric acid (10 ml) in order to prepare the diazonium salt. The resultant solution was added dropwise during 30 minutes to a cooled (4° C.) slurry of cuprous thiomethoxide (11.7 g) in water (20 ml) and the reaction mixture was stirred for 1.5 hours at ambient temperature.

The reaction mixture was extracted well with chloroform (a total of 650 ml) and the chloroform extracts were washed with 2 Normal hydrochloric acid (2×25 ml), dried (magnesium sulphate) and evaporated under reduced pressure to a residue. The residue was dissolved in dilute aqueous sodium hydroxide and 2 Normal hydrochloric acid was added to precipitate 4-methylthio-2-nitrobenzoic acid (3.71 g) m.p. 172.5° C.

b) A stirred solution of 4-methylthio-2-nitrobenzoic acid (4.56 g) and thionyl chloride (2.77 g) in benzene (65 ml) was heated under reflux for 1.5 hours. Aqueous ammonia (10 ml) was added dropwise to the stirred cooled (<5° C.) reaction mixture, which was then stirred with cooling for 45 minutes. Benzene was removed under reduced pressure and the residual solid was washed with water and recrystallised to yield 4-methylthio-2-nitrobenzamide, (2.35 g), m.p. 176°-8° C.

c) A stirred mixture of 4-methylthio-2-nitrobenzamide (2.47 g), stannous chloride dihydrate (13.13 g) and ethanol (90 ml) was heated under reflux under nitrogen for one hour. The reaction mixture was added to ice and neutralized to pH 7 with 5% aqueous sodium bicarbonate solution and the resultant mixture was extracted with ethyl acetate: methanol (9:1, 6×100 ml). The combined extracts were washed with brine, dried (magnesium sulphate) and evaporated under reduced pressure to yield 2-amino-4-methylthiobenzamide (1.84 g), m.p. 172.5°-173.5° C.

d) A solution of 2-propoxybenzoyl chloride (0.76 g) in acetonitrile (6 ml) was added dropwise to an ice-cold stirred mixture of 2-amino-4-methylthiobenzamide (0.70 g) and triethylamine (0.39 g) in acetonitrile (6 ml). The reaction mixture was stirred at ambient temperature for 17 hours. Acetonitrile was removed under reduced pressure and the residual solid was washed with water and recrystallised from ethanol to yield 4-methylthio-2-(2-propoxybenzamido)benzamide (0.49 g), m.p. 178.5°-181° C. A further sample (0.40 g, m.p. 182°-4° C.) was prepared by evaporating the ethanolic mother liquor and recrystallising the residue from ethanol.

e) A stirred solution of 4-methylthio-2-(2-propoxybenzamido)benzamide (0.85 g) and pyridine (1 ml) in 2 Normal aqueous sodium hydroxide was heated under reflux for 2 hours. The cooled reaction mixture was acidified with concentrated hydrochloric acid and the resultant mixture was extracted with chloroform (3×25 ml). The combined extracts were washed with water and then brine, dried (magnesium sulphate) and evaporated under reduced pressure to yield a solid which was recrystallised from ethanol to yield the title compound, 0.61 g, m.p. 156.5°-158.5° C.

EXAMPLE 3

7-Nitro-2-(2-Propoxyphenyl)-4(3H)-quinazolinone

Methyl 4-nitroanthranilate (2.0 g, prepared from 4-nitroanthranalic acid by treatment with dry HCl in refluxing methanol) was added to a solution of 2-propoxybenzoyl chloride (2.0 g) and triethylamine (1.0 g) in dry tetrahydrofuran (5 ml) at 0° C. After stirring at room temperature for 60 minutes, water was added and the mixture partitioned between water and dichloromethane. The organic layer was separated, dried (magnesium sulphate) and evaporated to give a solid (3.6 g). This material (1.0 g) was dissolved in 50 ml of saturated methanolic ammonia and the solution heated in a pressure vessel at 100° C. for 18 hours. Evaporation of the solvents and recrystallisation of the residue from dichloromethane-petroleum ether gave 7-nitro-(2-propoxyphenyl)-4(3H)-quinazolinone, 0.9 g, m.p. 138° C.

EXAMPLE 4

7-Amino-2-(2-Propoxyphenyl)-4(3H)-quinazolinone

A stirred solution of 7-nitro-2-(2-propoxyphenyl)-4(3H)-quinazolinone (3.0 g) in dry methanol (450 ml) was treated sequentially under a carbon dioxide atmosphere with 5% Pd/C (1.5 g) and anhydrous ammonium formate (2.8 g). After 60 minutes solids were removed by filtration and the filtrate evaporated to dryness. The residue was partitioned between water and dichloromethane, the organic layer separated, dried (magnesium sulphate) and evaporated. The residue was recrystallised from diethyl ether-petroleum ether to give 7-amino-2-(2-propoxyphenyl)-4(3H)-quinazolinone, 2.7 g, m.p. 185° C.

EXAMPLE 5

7-Methylamino-2-(2-Propoxyphenyl)-4(3H)-quinazolinone 7-amino-2-(2-propoxyphenyl)-4(3H)-quinazolinone (0.5 g) was heated under reflux in trimethylorthoformate (5 ml) for 22 hours. The reaction mixture was evaporated to dryness, the residue dissolved in dry tetrahydrofuran and treated with sodium borohydride (0.3 g) and 4A molecular sieves for 24 hours. The reaction mixture was partitioned between water and dichloromethane, the organic layer separated, dried (magnesium sulphate) and evaporated. The residue was recrystallised from dichloromethane-diethyl ether to give 7-methylamino-2-(2-propoxyphenyl)-4(3H)-quinazolinone 0.17 g, m.p. 204°-205° C.

EXAMPLE 6

Pharmaceutical compositions for oral administration are prepared by combining the following:

| | % w/w | | |
|---|---|---|---|
| 2-(2-Propoxyphenyl)quinazolin-4(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 7

A pharmaceutical composition for parenteral administration is prepared by dissolving the title compound of Example 4 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of the formula (1):

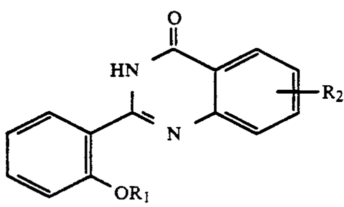

or a pharmaceutically acceptable salt thereof, wherein $R^1$ is $C_{1-6}$alkyl, $C_{2-6}$alkenyl, $C_{3-5}$cycloalkyl$C_{1-4}$alkyl, phenyl $C_{1-4}$alkyl or $C_{1-4}$alkyl substituted by 1 to 6 fluoro groups;

$R^2$ is hydrogen, $C_{1-6}$alkyl, $C_{1-6}$ alkylthio, $C_{1-6}$alkoxy, nitro or $-NR^3R^4$; and $R^3$ and $R^4$ are independently hydrogen or $C_{1-4}$alkyl optionally substituted by hydroxy provided that the carbon atom adjacent to the nitrogen atom is not substituted by hydroxy;

with the proviso that $R^1$ is not methyl when $R^2$ is hydrogen and $R^1$ is not ethyl when $R^2$ is hydrogen or 6-methyl.

2. A compound according to claim 1 wherein $R^1$ is $C_{2-5}$alkyl.

3. A compound according to claim 1 wherein $R^1$ is $C_{3-5}$alkenyl.

4. A compound according to claim 1 wherein $R^2$ is hydrogen or $C_{1-6}$alkyl.

5. A compound according to claim 1 wherein $R^2$ is $C_{1-6}$alkylthio or $C_{1-6}$alkoxy.

6. A compound according to claim 1 wherein $R^2$ is nitro or $-NR^3R^4$.

7. A compound according to claim 1 which is
2-(2-propoxyphenyl)quinazolin-4(3H)-one,
7-methylthio-2-(2-propoxyphenyl)quinazolin-4(3H)-one,
7-nitro-2-(2-propoxyphenyl)-4(3H)-quinazolinone,
7-amino-2-(2-propoxyphenyl)-4(3H)-quinazolinone, or
7-methylamino-2-(2-propoxyphenyl)-4(3H)-quinazolinone
or a pharmaceutically acceptable salt thereof.

8. A pharmaceutical composition which comprises a compound according to claim 1 or 2-(2-methoxyphenyl)quinazolin-4(3H)-one and a pharmaceutically acceptable carrier.

9. A method of effecting bronchodilation in a host in need thereof by administration of a non-toxic but effective amount of a compound of the formula (1):

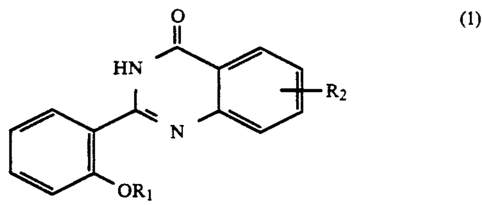

or a pharmaceutically acceptable salt thereof, wherein $R^1$ is $C_{1-6}$alkyl, $C_{2-6}$alkenyl, $C_{3-5}$cycloalkyl$C_{1-4}$alkyl, phenyl $C_{1-4}$alkyl or $C_{1-4}$alkyl substituted by 1 to 6 fluoro groups;

$R^2$ is hydrogen, $C_{1-6}$alkyl, $C_{1-6}$ alkylthio, $C_{1-6}$alkoxy, nitro or $-NR^3R^4$; and $R^3$ and $R^4$ are independently hydrogen or $C_{1-4}$alkyl optionally substituted by hydroxy provided that the carbon atom adjacent to the nitrogen atom is not substituted by hydroxy.

* * * * *